(12) United States Patent  
Edwards et al.

(10) Patent No.: US 9,131,979 B2  
(45) Date of Patent: *Sep. 15, 2015

(54) INTEGRATED BLADE ASSEMBLY AND IDENTIFICATION CIRCUIT

(71) Applicant: GYRUS ACMI, INC., Southborough, MA (US)

(72) Inventors: Kevin C. Edwards, Olive Branch, MS (US); Jay A. Casey, Memphis, TN (US); Vlad Bluvshtein, Plymouth, MN (US); Lori E. Lucke, Rosemount, MN (US); Dan W. Vahle, Minneapolis, MN (US); Moussa Sane, Collierville, TN (US); David C. Church, Millington, TN (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/583,977

(22) Filed: Dec. 29, 2014

(65) Prior Publication Data

US 2015/0112334 A1 Apr. 23, 2015

Related U.S. Application Data

(63) Continuation of application No. 13/803,380, filed on Mar. 14, 2013, now Pat. No. 8,956,355.

(60) Provisional application No. 61/731,919, filed on Nov. 30, 2012, provisional application No. 61/769,480, filed on Feb. 26, 2013.

(51) Int. Cl.  
*A61B 18/18* (2006.01)  
*A61B 18/14* (2006.01)  
(Continued)

(52) U.S. Cl.  
CPC .......... *A61B 18/149* (2013.01); *A61B 17/32002* (2013.01); *A61B 17/320016* (2013.01);  
(Continued)

(58) Field of Classification Search  
CPC ................. A61B 17/320016; A61B 17/32002; A61B 18/1402; A61B 18/1482; A61B 18/149; A61B 2017/0046; A61B 2017/00464; A61B 2017/00473; A61B 2017/00482; A61B 18/1206; A61B 18/14; A61B 19/5244; A61B 2018/1253; A61B 2018/126  
See application file for complete search history.

(56) References Cited

U.S. PATENT DOCUMENTS

| 3,223,088 A | 12/1965 | Barber et al. |
| 3,955,284 A | 5/1976 | Balson |

(Continued)

FOREIGN PATENT DOCUMENTS

| EP | 1201196 A1 | 5/2002 |
| EP | 2044893 A2 | 4/2009 |

(Continued)

OTHER PUBLICATIONS

PKS Cutting Forceps, General Surgery Products, Gyrus ACMI, An Olympus Company, available at www.gyrusacmi.com/user/display.cfm?display=product&pid=9063&catud=69&mainacat=General, last accessed and downloaded on Oct. 18, 2012.

(Continued)

*Primary Examiner* — George Manuel  
(74) *Attorney, Agent, or Firm* — The Dobrusin Law Firm, P.C.

(57) ABSTRACT

An interchangeable tip comprising: a stylet; a blade module including: an enclosure that electrically connects, signally connects, or both the interchangeable tip to a power source, a signal source, or both; and blade circuitry having: one or more control buttons, one or more switches, or both for controlling operation one or more functions of the interchangeable tip.

26 Claims, 9 Drawing Sheets

(51) Int. Cl.
  *A61B 17/32*  (2006.01)
  *A61B 18/12*  (2006.01)
  *A61B 19/00*  (2006.01)
  *A61B 17/00*  (2006.01)

(52) U.S. Cl.
  CPC ............ *A61B18/1206* (2013.01); *A61B 18/14* (2013.01); *A61B 18/1402* (2013.01); *A61B 18/1482* (2013.01); *A61B 19/5244* (2013.01); *A61B 2017/0046* (2013.01); *A61B 2017/00464* (2013.01); *A61B 2017/00473* (2013.01); *A61B 2017/00482* (2013.01); *A61B 2018/126* (2013.01); *A61B 2018/1253* (2013.01)

(56) References Cited

U.S. PATENT DOCUMENTS

| | | | |
|---|---|---|---|
| 4,014,342 A | 3/1977 | Staub et al. | |
| 4,878,493 A | 11/1989 | Pasternak et al. | |
| 5,112,299 A | 5/1992 | Pascaloff | |
| 5,230,704 A | 7/1993 | Moberg et al. | |
| 5,275,609 A | 1/1994 | Pingleton et al. | |
| 5,352,222 A | 10/1994 | Rydell et al. | |
| 5,376,078 A | 12/1994 | Dinger et al. | |
| 5,395,312 A | 3/1995 | Desai | |
| 5,405,348 A | 4/1995 | Anspach et al. | |
| 5,413,556 A | 5/1995 | Whittingham | |
| 5,492,527 A | 2/1996 | Glowa et al. | |
| 5,540,708 A | 7/1996 | Lim et al. | |
| 5,560,373 A | 10/1996 | DeSantis | |
| 5,569,254 A | 10/1996 | Carlson et al. | |
| 5,609,573 A | 3/1997 | Sandock | |
| 5,620,415 A | 4/1997 | Lucey et al. | |
| 5,620,447 A | 4/1997 | Smith et al. | |
| 5,712,543 A | 1/1998 | Sjostrom | |
| 5,792,167 A | 8/1998 | Kablik et al. | |
| 5,810,809 A | 9/1998 | Rydell | |
| 5,814,044 A | 9/1998 | Hooven | |
| 5,849,023 A | 12/1998 | Mericle | |
| 5,873,886 A | 2/1999 | Larsen et al. | |
| 5,899,915 A | 5/1999 | Saadat | |
| 5,904,681 A | 5/1999 | West, Jr. | |
| 6,010,476 A | 1/2000 | Saadat | |
| 6,042,593 A | 3/2000 | Storz et al. | |
| 6,053,923 A | 4/2000 | Veca et al. | |
| 6,074,386 A | 6/2000 | Goble et al. | |
| 6,152,941 A | 11/2000 | Himes et al. | |
| 6,217,598 B1 | 4/2001 | Berman et al. | |
| 6,221,088 B1 | 4/2001 | Bays | |
| 6,246,638 B1 | 6/2001 | Zook et al. | |
| 6,293,957 B1 | 9/2001 | Peters et al. | |
| 6,296,638 B1 | 10/2001 | Davison et al. | |
| 6,454,782 B1 | 9/2002 | Schwemberger | |
| 6,494,892 B1 | 12/2002 | Ireland et al. | |
| 6,716,215 B1 | 4/2004 | David et al. | |
| 6,752,816 B2 | 6/2004 | Culp et al. | |
| 6,824,550 B1 | 11/2004 | Noriega et al. | |
| 6,979,332 B2 | 12/2005 | Adams | |
| 7,179,255 B2 | 2/2007 | Lettice et al. | |
| 7,237,990 B2 | 7/2007 | Deng | |
| 7,247,161 B2 | 7/2007 | Johnston et al. | |
| 7,276,074 B2 | 10/2007 | Adams et al. | |
| 7,416,539 B2 | 8/2008 | Johnston et al. | |
| 7,442,191 B2 | 10/2008 | Hovda et al. | |
| 7,608,048 B2 * | 10/2009 | Goldenberg | 600/564 |
| 7,674,263 B2 | 3/2010 | Ryan | |
| 8,109,956 B2 | 2/2012 | Shadeck | |
| 8,202,288 B2 | 6/2012 | Adams et al. | |
| 2001/0047183 A1 | 11/2001 | Privitera et al. | |
| 2002/0038129 A1 | 3/2002 | Peters et al. | |
| 2002/0165549 A1 | 11/2002 | Owusu-Akyaw et al. | |
| 2003/0097129 A1 | 5/2003 | Davison et al. | |
| 2003/0165794 A1 | 9/2003 | Matoba | |
| 2004/0010258 A1 | 1/2004 | Carusillo et al. | |
| 2004/0167427 A1 | 8/2004 | Quick et al. | |
| 2004/0243163 A1 | 12/2004 | Casiano et al. | |
| 2005/0222566 A1 | 10/2005 | Nakahira | |
| 2005/0277970 A1 | 12/2005 | Norman et al. | |
| 2006/0259055 A1 | 11/2006 | Thorne et al. | |
| 2009/0270896 A1 | 10/2009 | Sullivan et al. | |
| 2010/0298763 A1 | 11/2010 | Adams et al. | |
| 2010/0317998 A1 | 12/2010 | Hibner et al. | |
| 2011/0009856 A1 | 1/2011 | Jorgensen et al. | |
| 2011/0017801 A1 | 1/2011 | Zemlok | |
| 2011/0066142 A1 | 3/2011 | Tal et al. | |
| 2011/0301578 A1 | 12/2011 | Muniz-Medina et al. | |
| 2012/0191117 A1 | 7/2012 | Palmer et al. | |
| 2012/0221035 A1 | 8/2012 | Harvey | |
| 2013/0004595 A1 | 1/2013 | Bhatia | |

FOREIGN PATENT DOCUMENTS

| | | |
|---|---|---|
| EP | 2133028 A2 | 12/2009 |
| GB | 2470607 A | 12/2010 |
| WO | 96/37156 A1 | 11/1996 |
| WO | 97/23169 A1 | 7/1997 |
| WO | 98/38932 A1 | 9/1998 |

OTHER PUBLICATIONS

GYRUS ACMI; Handpiece Cleaning and Maintenance Jun. 1, 2006.
Potentially Related Patent Application, U.S. Appl. No. 13/804,308, filed Mar. 14, 2013.
Potentially Related Patent Application, U.S. Appl. No. 13/796,416, filed Mar. 12, 2013.
Potentially Related Patent Application, U.S. Appl. No. 13/826,892, filed Mar. 14, 2013.
International Search Report and Written Opinion, Application No. PCT/US2013/077758, dated Mar. 25. 2014.

* cited by examiner

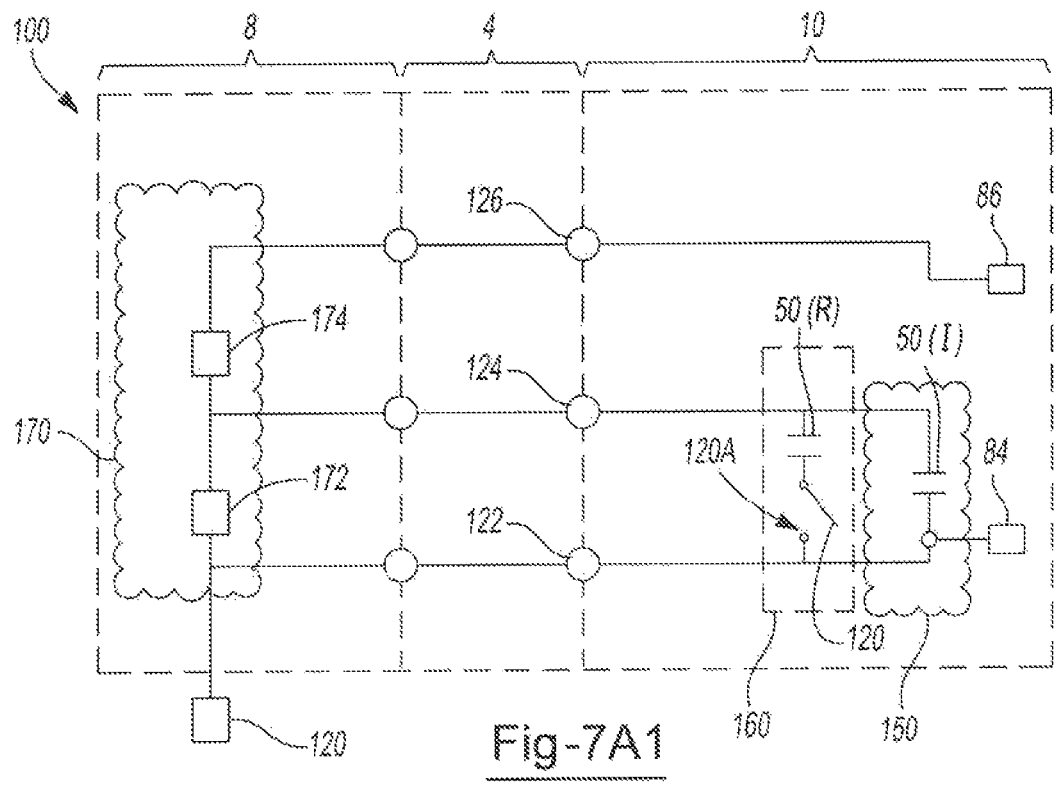
Fig-7A1
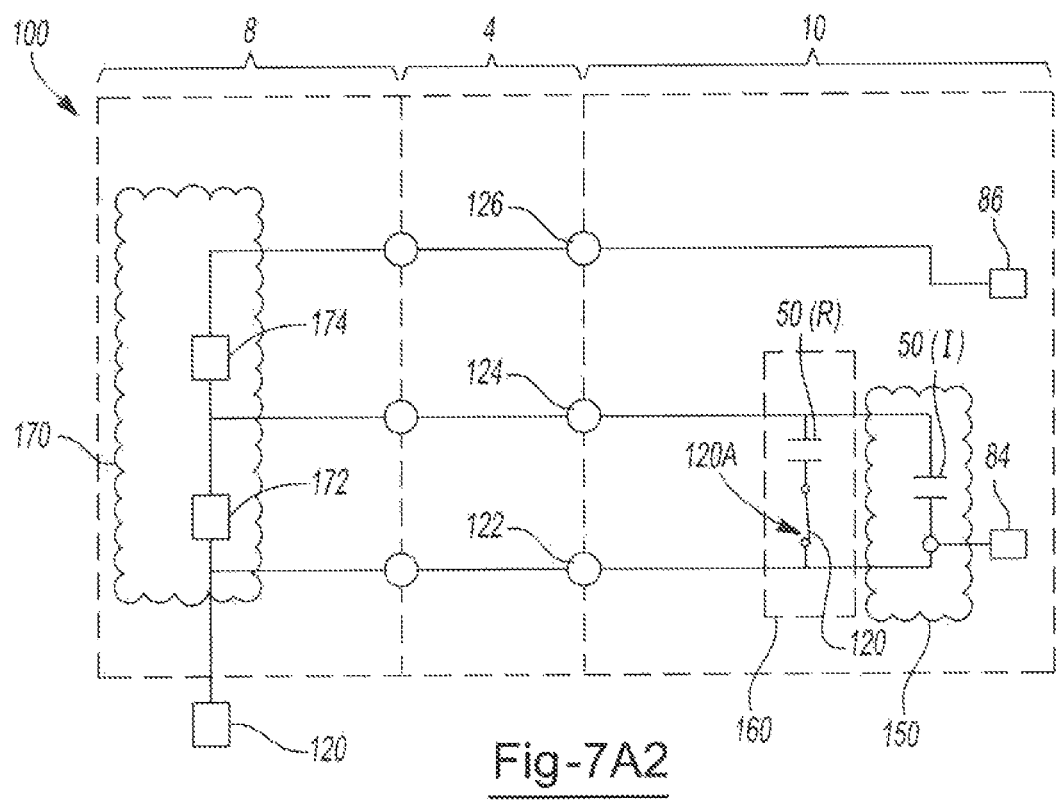
Fig-7A2

INTEGRATED BLADE ASSEMBLY AND IDENTIFICATION CIRCUIT

FIELD

The present teachings generally relate to a debrider blade module, and more specifically a debrider blade module with an integrated identification circuit.

BACKGROUND

Generally, debriders include a handpiece and a cutting portion. The handpiece includes motor that rotates one or more rotating, parts in the cutting portion. The cutting portion includes a cutting window where the cutting window exposes a cutting blade. The cutting blade is used to remove tissue, cartilage, bone, or a combination thereof. The cutting blade during use may result in bleeding and the cutting blade may include an energy source to perform electrosurgery. Typically, each debrider includes an integral tip, and during use a user selects a debrider based upon the intended use of the debrider such as coagulation, suction, cutting, cauterization, or a combination thereof. Generally, each handpiece is only usable with, one style of tip so that a different style tip cannot be installed in a handpiece and the debrider used for a different purpose or to perform a different function. Some tips may be used with multiple handpieces; however, some of the functionality may not work or may not work properly when installed in a different handpiece.

Further, most of the electrical components of a debrider are large (i.e., not conductive for placement in a handheld device) and/or fragile such that the components are located as far away from the operation site as possible and/or the components are housed in a protective chamber so that the components are too bulky to be located in the debrider. Moreover, these components when located in parts of the debrider may be subjected to contact with fluids which may cause a short and/or damage the components so that one or more functions of the debrider may be compromised. Additionally, when one or more of the debrider parts are cleaned after use and the cleaning process may damage the electrical components. For example, a typical method of cleaning is placing the debrider components in an autoclave and heating the components for a predetermined amount of time and then placing the components in a fluid to rapidly cool the components. This rapid heating and rapid coding may damage the electrical components and thus these electrical components may not be readily placed in parts of the debrider that may be cleaned.

Examples of some surgical instruments may be found in U.S. Pat. Nos. 5,810,809; 5,814,044; 5,904,681; 5,899,915; 6,074,386; 5,752,816; 6,979,332; 7,237,990; and 7,674,263 all of which are incorporated by reference herein for all purposes. It would be attractive to have interchangeable tips that can be installed in a handpiece and all of the functionality of each tip works without any user input. It would be attractive to have an interchangeable tip that includes an identification circuit in the interchangeable tip so that the interchangeable tip communicates with the handpiece and adjoining circuitry so that the adjoining circuitry controls each interchangeable tip based upon the identification circuit. It would be attractive to have a control switch in the interchangeable tip that controls one or more functions of the interchangeable tip. What is needed is an interchangeable tip that includes circuit elements that may be subjected to fluids during debriding and the circuit elements function properly and/or protect a user from shock due to any shorts caused by the fluid.

SUMMARY

The present teachings meet one or more of the present, needs by providing: an interchangeable tip comprising: a stylet; a blade module including: an enclosure that electrically connects, signally connects, or both the interchangeable tip to a power source, a signal source, or both; and bade tip circuitry having one or more control buttons, one or more switches, or both for controlling operation one or more functions of the interchangeable tip.

Another possible embodiment of the present teachings comprises: an interchangeable tip comprising: a stylet; a blade module including: an enclosure that electrically connects, signally connects, or both the interchangeable tip to power source, a signal source, or both; and blade circuitry including an identification circuit; wherein the blade circuitry provides a signal to a controller, control module, generator, or a combination thereof so that the controller, the control module, the generator, or a combination thereof determines one or more functions of the interchangeable tip, and wherein the stylet is free of electrodes.

Another possible embodiment of the present teaching comprises: an interchangeable tip comprising: a stylet; blade module including: a connection enclosure and a control enclosure including two or more pins; wherein a signal across the two or more pins have a capacitance of zero.

Yet another possible embodiment of the teachings comprises: a method comprising: inserting an interchangeable tip of the teachings herein into a handpiece; providing a signal to the handpiece and the interchangeable tip; and detecting a capacitance generated by the interchangeable tip in response to the step of providing the signal; wherein the step of detecting determines whether the interchangeable tip is configured to provide bipolar energy, monopolar energy, no power, or a combination thereof.

The teachings herein provide an interchangeable tip that can installed in a handpiece and all of the functionality of each tip works without any user input. The teachings herein provide an interchangeable op that includes an identification circuit in the interchangeable tip so that the interchangeable tip communicates with the handpiece and adjoining circuitry so that the adjoining circuitry control each interchangeable tip based upon the identification circuit. The teachings herein provide a control switch in the interchangeable tip that controls one or more functions of the interchangeable tip. The teachings herein provide an an interchangeable tip that includes circuit elements that may be subjected to fluids during debriding and the circuit elements function properly and/or protect a user from shock due to any shorts caused by the fluid.

BRIEF DESCRIPTION OF THE DRAWINGS

FIG. 5A illustrates a cross, sectional view of the interchangeable tip of FIG. 2 along lines 6-6;

FIG. 7A1 illustrates a circuit diagram representing the configuration of the interchangeable tip of FIG. 6A when the control circuit is open;

FIG. 7A2 illustrates the circuit diagram of FIG. 7A1 when the circuit is closed;

DETAILED DESCRIPTION

Figure 1:
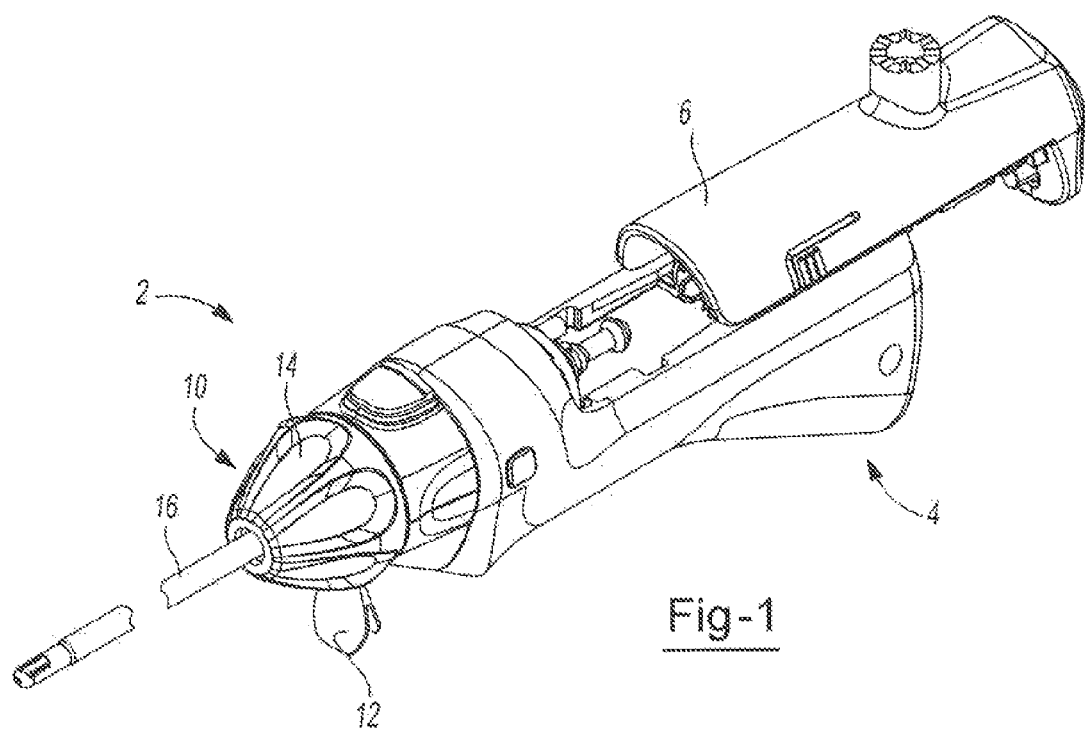
FIG. 1 illustrates a perspective view of a microdebrider inch ing an interchangeable tip.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein provide a debrider and preferably a microdebrider. The debrider generally includes a handpiece and a separable blade assembly (i.e., an interchangeable tip). The handpiece includes an aperture that receives a portion of the blade assembly so that the handpiece may drive the blade assembly during use. The handpiece may include a motor and one or more gears that drive one or more rotary cutting tubes of the blade assembly (i.e., stylet). Other teachings of the handpiece may be gleaned from the teachings herein including those of paragraph Nos. 6-8, 26-45, 061-062, 065, and 70-72 and FIGS. 1-3 of U.S. Patent Application Ser. No. 61/731,919 filed on Nov. 30, 2012 teaching a handpiece and one or more connection portions for driving the separable blade assembly, the teachings of which are expressly incorporated by reference herein regarding the handpiece and physical connection and electrical connection with the interchangeable tube and its venous components. The handpiece and blade assembly may be separable so that the handpiece, the blade assembly, or both may be cleaned, disposed, or both after use.

Preferably, the blade assembly (e.g., an interchangeable tip) may be disposable. The blade assembly includes a tip and a mechanical enclosure. The blade assembly includes a stylet (i.e., one or more tubes). For example, the interchangeable tip may include an inner tube, and intermediate tube, an outer tube, or a combination thereof. The blade assembly may include one or more tubes and preferably two or more tubes. The one or more tubes may be made of any biocompatible material. The one or more tubes may be made of a material that may be used to perform surgery. The one or more tubes may be made of any material that is sufficiently rigid to perform surgery; to be pushed, pulled, angled, or a combination thereof without bending, breaking; or both. The one or more tubes may be made of a material that conducts electricity. The one or more tubes may be made of a polymer, metal, a natural material, a synthetic material, or a combination thereof. Preferably, the one or more tips are made of stainless steel or a surgical steel. Preferably, the stylet may include at least an outer tube and an inner tube. The stylet may include an outer tube, an intermediate tube at least partially disposed within the outer tube, and an inner tube at least partially disposed within the intermediate tube and the outer tube. Each of the two or more tubes may be connected. Preferably, each of the two or more tubes are axially independent of each other so that one or more of the tubes may rotate without rotating the other tubes. For example, an inner tube, an intermediate tube, or both may rotate inside of the outer tube. The two or more tubes may rotated relative to each other and the rotation of the tubes may be monitored by a sensor in the blade assembly, the handpiece, or both by two or more transmitters, magnets, an encapsulation connector, or a combination thereof located in the blade module (i.e., mechanical enclosure) of the blade assembly, the handpiece, or both. Other teachings regarding the encapsulation connector, the two or more transmitters, the magnetic communication, or a combination thereof may be gleaned from the teachings herein, including those of Paragraph Nos. 008-0014 and 0035-0055; and FIGS. 2-14 of U.S. patent application Ser. No. 13/251,493, filed on Oct. 3, 2011, incorporated by reference herein for all purposes regarding the encapsulation connector, the two or more transmitters, the magnetic communication, or a combination thereof. Alternatively, other teachings regarding rotating one or more of the tubes relative to each other may be gleaned from the teachings herein, including those of Paragraph Nos. 004-005, 0012-0038 and FIGS. 1A-4C of U.S. patent application Ser. No. 13/796,412, filed on Mar. 12, 2013, incorporated by reference herein for all purposes regarding a lock selector, bias device, and an actuation selector.

The one or more tubes may be straight, angled, bent, curved, flex-jointed (e.g., if the outer tube is bent then inner tube may be flexible to spin), or a combination thereof. The one or more tubes may form one or more angles and the one or more angles may be any angle or combination of angles, include an angled portion, or both. The angled portion may be a rigid bend, an arcuate bend, a sweeping curve, or a combination thereof. The one or more tubes may extend from a blade module that includes a mechanical enclosure and form an angle so that the one or more tubes may be used to perform a surgical procedure or be used in a predetermined location.

The blade module may be any device that houses one or more moving parts of the disposable blade, a portion one or more of the one or more blades extends through, or a combination thereof. The blade module may include a fixed portion that the user grips, a rotatable portion, or both. The blade module may include a mechanical enclosure enclosure) that houses one or more moving parts, switches, controls, user inputs, circuit boards, circuit board components, or a combination thereof. The enclosure may be fixed relative to the nosecone, a collet, the handpiece, or a combination thereof. The enclosure may include one or more functional buttons. Preferably, the enclosure includes at least a control enclosure and a connection enclosure that each form a portion of the enclosure. The enclosure may include a seat that forms a movable connection, a pivotable connection, or both with a lock lever so that the lock lever may be moved between a locked position and an unlocked position. Other teachings regarding the lock lever, components moved by the lock lever (e.g., locking spline), a collet nosecone, internal gearing (e.g., pinion gears or nosepiece gears), or a combination thereof may be gleaned from the teachings herein, including those of Paragraph Nos. 005-007 and 0029-0054; and FIGS. 1-14 and related description in paragraph Nos. 0055-0070 of U.S. Patent Application Ser. No. 61/769,480, filed on Feb. 26, 2013, incorporated by reference herein for all purposes regarding a lock lever, components moved by the lock lever, the collet, the nosecone, and the internal gearing. Preferably, the lock lever is movably connected to the connection enclosure.

The connection enclosure may be any part of the interchangeable tip that connects to a power source so that power is supplied to the interchangeable tip. The connection enclosure may be water resistant, may protect the circuitry from contact with a fluid, or both. The connection enclosure may be sufficiently sealed so that the connection enclosure isolates one more devices used to transmit a signal, transmit power, one or more electrical circuits, or a combination thereof in the presence of a fluid so that a short is prevented and/or substantially reduced. The connection enclosure may directly connect to the power source. Preferably, the connection enclosure directly, connects to the handpiece and power is supplied to the interchangeable tip through the handpiece. The connection enclosure may be any part of the interchangeable tip that forms a connection and assists in providing control signals between the interchangeable tip and the handpiece, a generator; a control module, or a combination thereof. The connection enclosure may include one or more plugs that electrically connect the interchangeable tip to a handpiece, a power source, or both. Preferably, the one or more plugs include one or more connection pins so that power, signals (e.g., control signals, electrical signals, the like, or a combination thereof), or both are communicated between one or more components that are in electrical communication, signal communication, or both with the interchangeable tip.

Each plug may include any number of pins so that the interchangeable tip performs a desired function, provides communication with an adjacent component (e.g., handpiece, generator, control module, or a combination thereof), is free of user input to configure one or more of the desired functions, or a combination thereof. For example, upon a user placing an interchangeable tip into a handpiece the generator, controller, control module, or a combination thereof may automatically use the detection circuit to detect the interchangeable tip. Each plug include one or more pins, two or more pins, or three or more pins. Each plug May include 5 or less pins or 4 or less pins. One or more of the plugs may be free of a pin. One or more of the plugs may be free of a pin so that the interchangeable tip may be free of power, free of signals, or both. Preferably, each of the pins are electrically segregated. For example, the plug may consist of three discrete plug portions and two of the plug portions may include a iii and one of the plug portions may be free of a pin. The plug may include discrete pockets for housing each of the pins. The plug may be a recess and may receive a portion of an adjacent component such as the handpiece. Preferably, the plug is a projection and extends into an adjacent component so that an electrical connection, a signal connection, or both is formed inside of an adjacent component (e.g.; a handpiece). More preferably, the plug may be configured to protect the one or more pins from a fluid. A connection formed between the plug and an adjacent handpiece may be sufficiently sealed so that the pins, wires, or both extending between the plug and the handpiece are isolated so that the connection prevents energy from being transferred to a patient, a user, both. The plug may assist in aligning the interchangeable tip when attaching the interchangeable tip to an adjacent component such as a handpiece.

The plug may have any shape and size so that the plug assists in forming an electrical connection; a signal connection, a connection to an adjacent component, or a combination thereof. The plug may be symmetrical, asymmetrical, oval, round, include a include a raised portion, or a combination thereof. The one or more pins may extend from the plug to an internal pocket in the connection enclosure.

The internal pocket may be any part of the connection enclosure that house the one or more ins; assists in connecting the one or more pins to a connector, providing power, providing signals, or both to the interchangeable handpiece or a combination thereof. Preferably, the internal pocket may be sized and shaped so that the connection pins align with an adjacent component and are in communication with the adjacent component. The internal pocket may have a shape that substantially mirrors the shape of a connector so that the connector is substantially self-aligned within the pocket, substantially self-aligned with the pins, or both. The internal pocket may assist in orienting the connection enclosure with the interchangeable tip during assembly. The internal pocket may be located proximate to one or more connection supports that assist in aligning the connector with the internal pocket, aligning the connection enclosure with the interchangeable tip, aligning the connection enclosure with the control enclosure, or a combination thereof.

The one or more connection supports may extend from the connector, the connection enclosure, the interchangeable tip, the control enclosure, or a combination thereof into a juxtaposed recess in the opposing component to assist in forming a fixed connection between the two adjacent components. Preferably, the connection enclosure may include two or more connection supports that extend into a recess in the interchangeable tip so that the connection enclosure aligns with the interchangeable tip and so that the connector is aligned with the one or more pins. More preferably, the connection enclosure includes one or more connection supports for connecting to a connector and one or more connection supports for connecting to a control enclosure, or vice versa. The connection enclosure may include one or more recesses, one or more connection supports, or a combination of both on each side forming a fixed connection with a control enclosure, which may include one or more opposing recesses, one or more opposing control supports, or a combination of both so that a connection is formed.

The control enclosure may be any component that allows a user to operate one or more functions of the interchangeable tip. Preferably, the control enclosure includes one or, more control buttons and/or one or more switches, provides access to one or more buttons and/or one or more switches; or both that control one or more of the functions discussed herein. The control enclosure may enclose and protect all or a portion of a circuit, internal components, switches, or a combination thereof. The connection enclosure may be sufficiently sealed so that the connection enclosure isolates one more devices used to transmit a signal, transmit power, one or more electrical circuits, or a combination thereof in the presence of a fluid so that a short is prevented and/or substantially reduced. Preferably, the control enclosure may protect all or a portion of a circuit, internal components, one or more switches, or a combination thereof, while allowing a user to actuate the one or more switches so that one or more functions may be operated. For example, the control enclosure may include a flexible polymeric portion that is resistant to penetration of a fluid. All or a portion of the control enclosure may be malleable, compressible, movable, or a combination thereof so that one or more control buttons may be actuated and protected by the control enclosure. Preferably, the control enclosure covers and protects blade circuitry while allowing a user to actuate one or more control buttons on the blade circuitry.

The blade circuitry may be any circuitry within the interchangeable tip that transmits to and/or accepts signals, power, or both from the handpiece, a generator, a control module, or a combination thereof. The blade circuitry rosy be connected to, run, control, or a combination thereof one or more functions of the interchangeable tip. The blade circuitry may transmit a signal to a control module, the handpiece, a generator, or a combination thereof indicating the type of interchangeable tip connected, the functionality of the interchangeable tip, or both. The blade circuitry may include one or more control buttons, one or more pins, one or more printed circuit boards, one or more sockets, one or more capacitors, or a combination thereof. Preferably, the blade circuitry includes a printed circuit board for connecting one or more functional components together, for controlling one or more functional components, for assisting in identifying the function of the interchangeable tip, or a combination thereof.

The printed circuit board nay be any component that may electrically connect, signally connect; or both, two or more adjacent functional components so that during operation the functional components, may perforce one or more predetermined functions. For example, the printed circuit board may receive and transmit signals to and from the handpiece, the generator, or both (i.e., be signally connected). In another example, the printed circuit board may receive and transmit power to and from the handpiece, the generator, or both (i.e., be electrically connected). The printed circuit board may be any device that may be used to identify the type of circuit, the type of interchangeable tip, or both. The printed circuit board may include, be connected to, form an intermediary connection piece, or a combination thereof so that the interchangeable tip may perform one or more of the functions discussed herein. For example, the printed circuit board may form one polarity of a connection and another component may form the other polarity of the connection so that when both polarities are activated power is supplied. Preferably, the printed circuit board is sufficiently small so that the printed circuit board is wholly housed within the blade module. More preferably, the printed, circuit board is sufficiently small so that the printed circuit board fits within the control enclosure. The printed circuit board may be sufficiently large so that the printed circuit board includes one or more control buttons, one or more capacitors, one or more sockets, or, a combination thereof. Preferably, the printed circuit board is sufficiently large so that one or more functional components are connected to the printed circuit board and operate one or more of the functions discussed herein. The printed circuit board may include one or more board components. For example, a board component may be one or capacitors, diodes, resistors, zenor diodes, an amplifier, a switch, or, a combination thereof. Preferably, at least one control button is electrically connected to and/or located on the printed circuit board, The one or more ore control button may be any control button that controls one or more functions of the interchangeable tip. The one or more control buttons may be a switch. The one or more control buttons may be any control button that may be actuated, moved, signalingly operated or a combination thereof by a user. The one or more control buttons may be connected to the printed circuit board and extend towards and/or into contact with a portion of the control enclosure so that during use a user can actuate the one more control buttons. The one or more control buttons when actuated may operate one or more functions of the interchangeable tip. Preferably, the one or more control buttons when actuated may close a circuit and allow monopolar energy and/or bipolar energy to pass through the stylet. The one or more control buttons may be used to control rotation of the inner tube, direction of rotation; type of rotation (i.e. oscillation, forward rotation, reverse rotation, or a combination thereof); or a combination thereof. Power, electrical signals, or both may be supplied to and/or from the control buttons via one or more pins.

The one or more pins may be any pin that assists in forming a connection. Each of the one or more pins may be an input. Each system may have one or more inputs, preferably two or more inputs, or even three or more inputs. The one or more pins may be a combination of fixed pins and spring pins. Preferably, at least some of the one or more pins may be spring pins. More preferably, the pins used to form a connection with one or more movable parts may be spring pins. The one or more spring pins may be any pin that supplies power, an electrical signal, a control signal, or a combination thereof to and/or from the blade module. The spring pin may be any pin that forms an electrical connection, a signal connection, or both with a moving part; between two moving parts, or both. The spring pin may include one or more movable parts. The one or more movable parts may move so that an electrical connection signal connection, or both are maintained as the spring pins moves, one or more of the tubes move (i.e., outer tube, intermediate tube, inner tube, or a combination thereof), or both. The spring pins may include a biasing member so that the staring pins may extend when not contacted and retract when contacted. The bias member may extend the spring pin with sufficient force so that the spring pin maintains a constant contact with an adjacent part (e.g., one or more of the tubes). The bias member may extend the spring pin so that the spring pin contacts an outer diameter of one or more of the tubes and maintains contact even if there is a change in diameter. Preferably, the bias member has sufficient strength and the spring pin has a sufficient length so that the bias member maintains each of the spring pins respectively in constant contact with the outer tube, the intermediate tube, or both during use. The one or more spring pins may be connected to a power source, a control signal, or both through one or more adjacent sockets.

The one or more sockets may be any device that connects a pin, a wire, an energy source, a signal source, or a combination thereof to a printed circuit board, a connector, the blade module, or a combination thereof. The one or more sockets may be any device that forms a fixed connection so that power, signals, or both may pass into, out of, through; or a combination thereof the blade module. The one or more sockets may be any device that forms a sealed connection with one or more wires, one or more pins, one or more connectors, one or more devices used to transmit power and/or a signal, or a combination thereof. The one or more sockets may be constructed so that the sockets preventing shorting of the electrical circuits, electrical connections, or both in the presence of fluids. The sockets may be located in and or on any device that forms an electrical connection, a signal connection, or both. One or more sockets may be located on and/or within a printed circuit board, a connector, at both. The one or more sockets may provide a fixed connection with a pin, a wire, an energy source, a signal source, or a combination thereof so that the signal is maintained during use. Preferably, at least one socket is located on the printed circuit board and at least one socket is located in connector. More preferably, two connectors are located on the printed circuit board opposite one or more capacitors.

The one or more capacitors may be any capacitor that provides a capacitance through the module. The capacitors may be any capacitor that is sufficiently large so that the capacitance of the capacitor may be measured in the handpiece, a generator, a control module, or a combination thereof. The capacitor may be located at any location within the circuitry of the blade module so that the capacitance the capacitors, a shift in capacitance, or both may be measured in the handpiece, at a generator, at a control module, or a combination thereof. The size, capacitance, or both of each capacitor may vary from application to application. Preferably, each type of interchangeable tip (e.g., each different functionality of a tip) has a different circuit capacitance that may be measured by the generator, handpiece, module, or a combination thereof. For example, the capacitors used may range from 5 nF to 100 nF, and each corresponding capacitance may be correlated to one or more functions in a look up table. The capacitors have a range beginning at about 1 pF or more, about 5 pF or more, about 10 pF or more, or about 15 pF or more. The capacitors may have a range ending at about 1 F or less, about 100 μF or less; 1 μF or less, or about 100 nF or less. The capacitors may be sufficiently sized so that the handpiece, generator, control module, or a combination thereof may identify the different interchangeable tips and respective functionality based only on the change in capacitance when a tip is connected, a circuit is electrically energized, signally energized, or a combination thereof. The difference in capacitance of each capacitor may be sufficiently identifiable so that the handpiece, generator, control module, or a combination thereof may reference the respective measured capacitance with a lookup table with repeatability, with precision, or both. The difference in capacitance used in each capacitor may be about 1 nF or more, about 5 nF or more, or about 10 nF or more. The difference in capacitance of each capacitor may be about 1000 nF or less about 500 nF or less, or about 100 nF or less. Preferably, the capacitors are located on the printed circuit board and electrically connected to the handpiece, the generator, the control module, or a combination thereof. Each circuit board may include at least two capacitors. In one example, a capacitor may be electrically connected in a discrete control loop such as a first loop for identification of the functions of a handpiece (i.e., identification capacitor) and a second capacitor (i.e., control capacitor) may be electrically connected in a second control loop that is used to activate one or more of the functions of the handpiece. However, the system may be completely free of capacitors for identification purposes and thus the system may have a zero and/or near zero capacitance. For example, two or more inputs, pins, or both may be shunted so that they are directly connected, forming an identification circuit without any capacitors. In another example, the system may be free of a control capacitor and only include an identification capacitor.

The one, or more identification capacitors may be any capacitor that has a capacitance that correlates to a predetermined value in a look up table so that the measured capacitance may be used to determine the functions that the interchangeable tip may perform, if a tip is present, or both. The one or more identification capacitors may be sufficiently large that the capacitance may be used to identify the functions of a provided interchangeable tip. The one or more identification capacitors may be located anywhere along the circuit board so that one or more signals may be passed through the identification capacitor to identify the type of interchangeable tip installed. The one or more identification capacitors may be in a loop in the circuit that may only provide a signal back to a generator, a control module, a handpiece, or a combination thereof so that the type of interchangeable tip maybe identified. The system may include a plurality of identification capacitors. Preferably, the system includes one identification capacitor. The one or more identification capacitors may be located in parallel, in series, or, both with one or more control capacitors.

The control capacitor may be any capacitor that provides a capacitance to the system when one or more switches, one or more control buttons, or both are actuated. For example, the system may have a first capacitance and when a switch is actuated that includes the control capacitor the capacitance measured may shift to a second capacitance. The control capacitor may change the capacitance of the system when a control loop containing the control capacitor is completed (e.g.; a circuit is closed so that the circuit is powered). The control capacitor may provide a capacitance to the system so that the system can determine if a reading is a true reading or a false reading. The control capacitor may provide a capacitance to the system and/or change the capacitance of the system only if the switch; control button, or both is actuated and a circuit is complete. The control capacitor may assist the generator in controlling one or more functions of the debrider so that the one or more functions are only aced upon a command by a user and not by a short. The control capacitor may be electrically connected, signally connected, or both so that if a portion of the interchangeable tip shorts, the detection circuit reads the switch as being open, shorted, broken, or a combination thereof, but a shift in capacitance is not measured so the system does not activate the function of the shorted switch. The one or more switches may not be activated when there is a short in the printed circuit board, a switch, or both. Preferably, the one more switches may not activate when a short, an incorrect impedance, an incorrect capacitance, or a combination thereof presented. The control capacitor may be configured within the circuit so that the control capacitor only changes the capacitance of the system when the switch, control button, or both are actuated (i.e., closed). The control capacitors may be electrically connected, signally connected, or both to the handpiece, the generator, the control module, or a combination thereof through one or more connectors so that the capacitance of the system is intermittently monitored and/or continuously monitored.

The one or more connectors may be any device that receives one or more pins and electrically connects, signally connects, or both the pins to an adjacent component. The one or, more connectors may be any device that assists in providing en electrical connection, a signal connection, or both between one or more pins and one or more tubes, one or more printed circuit boards, or both. Preferably, the one or more connectors assist in creating a connection with one or more tubes having varying diameters so that one or more functions of the device may be used. The one or more connectors may include one or more spring pins, one or more sockets, one or more pins, one or more connector supports, or a combination thereof so that the connector assists in creating one or more electrical connections, one or more signal connections, or both. The one or more connectors may form an intermediary between two electrical points, two signal points, or both. The connector may directly form an electrical connection, a signal connection, or both with an intermediate tube, an inner tube, or both. The connector may indirectly form an electrical connection, a signal connection, or both with the outer tube, the intermediate tube, or both. The connector may make one or more connections with the printed circuit board so that power is supplied to the printed circuit board. The connector may electrically isolate two or more electrical inputs, signal inputs, or both. The connector may assist in completing a circuit so that one or more functions of the interchangeable tip may be employed. The tone or more connectors may be connected to and/or form all or a portion of one or more electrodes.

The one or more electrodes may be any power supply point that provides power to the stylet. Preferably, the one or more electrodes provide power to the stylet so that the stylet may provide a monopolar energy source or a bipolar energy source. For example, an electrode may be comprised of one or more pins, a connector, one or more wires, a printed circuit board, and may provide power to one or more tubes of the stylet so that one or more of the tubes are energized. The electrode may be any device that provides power directly and/or indirectly to the stylet. The electrode may be any device that provides power from a handpiece to a stylet so that the stylet is energized. The electrode may be a wire that extends from a printed circuit board to a tube of the stylet. Preferably, an electrode is not a connector that directly extends between and electrically connects, signal connects, or both two adjacent input pins from a handpiece. For example, a first pin and a second pin may extend into the interchangeable tip and may be directly connected together so that a signal enters the tip via one pin and is immediately directed out of the tip via the other pin. In another example, two pins may be directly connected together via a shunt so that the connection is an identification circuit with a zero capacitance and the circuit is free of an electrode. Two pins directly connected together by a connector may form a circuit that is an identification circuit.

The circuit may be any circuit that controls one or more functions of the microdebrider. The circuit may be used to identify the functionality of the interchangeable tip. For example, the circuit may be, connected to a control module, a generator, or both that determines the functionality of the interchangeable tip based on one or more measured conditions of the circuit. The circuit may be signally connected to one or more look-up tables. The circuit may include one or more inputs. The one or more inputs may be an applied signal, applied power, or both so that a circuit is created. The circuit may include one or more outputs. The one or more outputs may be any portion of the circuit that returns a signal, returns power, powers a portion of the interchangeable tip, or a combination thereof. The one or more outputs preferably provide power from one or more of the pins to one or more of the tubes of the stylet. The one or more outputs may provide power from the circuit to a pin, a spring pin, or both to one of the tubes of the stylet. One or more of the outputs may be shunted.

The open circuit may be any circuit that is electrically blocked, signally blocked, or both so that power, a signal, or both extending to one or more tubes of the stylet from one or more adjacent components, one or more circuits, or a both does not reach the stylet. The open circuit may be any circuit that is terminated. The open circuit may be a blocked portion of the circuit. The open circuit may be an absence of one or more pins, one or more spring pins, or both so that an electrical connection, signal connection, or both is terminated. The open circuit may end an identification circuit, a control circuit, or both. The open circuit may terminate one or more identification portions and one or more control portions of a circuit. Preferably, an identification circuit is not an open circuit. For example, an identification portion (i.e., identification circuit) may provide electrical feedback, signal feedback, or both to a microprocessor, a generator, a controller, or a combination thereof so that the system identifies the functions of the interchangeable tip and the control portion (i.e., control circuit) may operate the one or more functions.

The identification portion (hereinafter identification circuit) of the circuit may be any portion that provides some feedback so that the functions of the interchangeable tip may be identified. The identification circuit may generate a signal that may be used to identify the functions of interchangeable tip, the type of interchangeable tip, the number of electrodes, or a combination thereof. The signal of the interchangeable tip may be any signal that may be used to identify the functions of the interchangeable tip. The signals may be any signal that the controller, control module, generator, or a combination thereof may use to power and/or control one or more functions of the interchangeable tip during use. Preferably, the signals are a shift in frequency caused by the identification circuit. For example, the signals may have a first frequency before a capacitor and a second frequency after exiting the capacitor. This frequency may be listed in a look up table (e.g., capacitance as discussed herein may refer to a frequency change based on passing through a capacitor). The identification circuit may be a loop connected between an input and an output of the circuit. The identification circuit may include only a capacitor between the input and the output of the circuit. The identification circuit may include one or more circuit board components. The circuit board components may include one or capacitors, diodes, resistors, zenor diodes, an amplifier, or a combination thereof. The identification circuit may be free of one or More of one or capacitors, diodes, resistors, zenor diodes, an amplifier, or a combination thereof. The identification circuit may be free of a switch or a control button. The identification circuit may remain closed once the interchangeable tip is connected with a handpiece so that identification of the one or more functions of the interchangeable tip may be measured. The one or more identification circuits may be in parallel, in series, or both with the one or more control circuits.

The one or more control portions (hereinafter control circuits) may be any circuit that controls one or more functions of the interchangeable tip. The one or more control circuits may be any circuit that may be opened and closed by a user so that one or more functions of the interchangeable tip may be turned on and off. The control circuit may be any circuit that includes a switch, a control button, or both that opens and closes so that one or more functions of the interchangeable tip may be turned on and off. The control circuit may include one or more circuit board components. The circuit board components may be of a capacitor, diode, resistor, zenor diode, an amplifier, or a combination thereof. The control circuit may be free of a capacitor, diode, resistor, tenor diode, an amplifier, or a combination thereof. Preferably, the control circuit includes a capacitor so that when the switch; the control button, or both are actuated the capacitance of the system changes. A capacitor of a control circuit may vary based upon the function of a given control circuit and the capacitance may be measured on a look up table so that the controller, the control module, the generator, or a combination thereof may verify the function being requested by actuation of the switch, the control button, or both. The control circuit may be electrically connected, signally connected, or both to an identification circuit, one or more inputs, or both. The one or more inputs may be any input that completes a circuit so that one or more functionalities may be employed, one or more functionalities may be identified, or both. Preferably, the control circuit includes one or more switches.

The one or more switches may be any switch that may switch between an identification circuit and an operation circuit. The one or more switches may activate a function. The one more switches may be a control button as discussed herein. The one or more switches may be any switch that closes a portion of the circuit creating a bypass, forming a circuit, or both. For example, when the switch is closed the signal, the power, or both may bypass an identification portion of the circuit and supply power, a signal, or both so that one or more functions of the interchangeable tip may be employed. The one or more switches when closed may supply power to the system, may change the capacitance of the system, may send a signal to a generator, a control module, or both so that one or more functions are powered.

The generator may be any device that is electrically connected, signally connected, or both to the interchangeable tip and assists in controlling one or more functions of the debrider, identifying one or more functions of the debrider, or both. The generator may include one or more control modules, one or more controllers, or both that monitor an identification circuit, one or more switches, a handpiece, an interchangeable tip, or a combination thereof so that one or more functions may be recognized, controlled, powered, or a combination thereof. The generator, the controller, the control module, or a combination thereof may include one or more algorithms that that continuously monitor, in real time, changes in the modes of operation (e.g., presence of an interchangeable tip; removable of an interchangeable tip; activation of monopolar energy; bipolar energy, or both; deactivation of monopolar energy, bipolar energy, or both; or a combination thereof). The algorithms may include one or more look up tables. The generator may be any device that intermittently monitors, continuously monitors, or both signal measurements, capacitance, or both of the system, the debrider, the interchangeable tip, or a combination thereof. Preferably, the generator continuously monitors signal measurements, capacitance, or both of the interchangeable tip so that the generator can adjust its settings to those of the interchangeable tip, provide a user with control options for the interchangeable tip, configure the system to run one or more functions of the interchangeable tip, or a combination thereof. The generator may include one or more detection circuits.

The one or more, detection circuits may be any circuit that detects a signal in the interchangeable tip. Preferably, the one or more detection circuits may be any circuit that detects a capacitance of the interchangeable tip to ascertain the functionality of the interchangeable tip, the use of the interchangeable tip, the componentry of the interchangeable tip, or a combination thereof. The detection circuit may include one or more control modules, one or more controllers, one or more microprocessors, or a combination thereof that monitor the signals of the interchangeable tip. The one more detection circuits may include one or more RF generators.

The one or more RF generators may be any device that may provide power, a sign or both to one or more circuits, one or more legs of a circuit, or a combination thereof. The one or more RF generators may provide a signal to the circuit so that the detection circuit may monitor the circuit for a capacitance, a change in capacitance, a shift in frequency, a change in impedance, or a combination thereof. The one or more RF generators may provide power to the circuit so that the tip may provide bipolar energy, provide monopolar energy, rotate, reciprocate, oscillate, or a combination thereof. The RF generator may provide power simultaneously to two legs; to one leg; to one leg and power a return lead; through one leg and provide power, a signal, or both through an identification circuit; to one leg and provide power, a signal, or both through a shunt; or a combination thereof. A signal, power, or both from the RF generator may go through the identification circuit, the control circuit, or both and be monitored by the generator, controller, control module, or a combination thereof and compared to predetermined values in one or more look up tables.

One or more look up tables may be located within the detection circuit, within the generator, within a control module of the detection circuit, within a controller in the detection circuit, or a combination thereof. Preferably, upon the detection circuit detecting a signal from the interchangeable tip the detection circuit compares the signal measurement (as, capacitance) to a list of signal measurements in the look up table and determines the functions of tip installed, the type of tip installed, or both. After detection of the interchangeable tip and comparing the signal measurements to the look up table the detection circuit may monitor the signals for the status of the one or more switches based upon the signal measurements, changes in the signal measurements, or a combination of both. The generator may be fully and/or partially located in the handpiece, may be a discrete piece fully and/or partially located outside of the handpiece, or a combination of both. The generator may power the interchangeable tip according to a function energized by a user, a function selected by a user, an identified function of the interchangeable tip, or a combination thereof. Preferably, the generator may power one or more desired functions.

The functions of the interchangeable tip may be any function selected by a user. The functions of the interchangeable tip may be any function that assists a user in performing a procedure. The functions may be applying monopolar energy, bipolar energy, non-energized, forward rotation, reverse rotation, oscillating rotation (e.g., forward and then reverse and vice versa), reciprocating (i.e., distal and then proximal and vice versa) high speed rotation, low speed rotation, non-rotational, or a combination thereof. Preferably, at least one of the functions of the interchangeable tip is rotating the inner tube (i.e., forward, reverse, or oscillating). Thus, in one example, the system includes one signal measurement, one capacitance, or both for a forward rotating interchangeable tip, a second signal measurement, a second capacitance, or both for a reverse rotating interchangeable tip, and a third signal measurement, a third capacitance, or both for an oscillation rotating interchangeable tip. In another example, a low speed forward rotating interchangeable tip with monopolar energy capabilities will have a different signal measurement, different capacitance, or both then a high speed oscillating bipolar energy interchangeable tip and these values will be listed in a look up table so that the generator, control module, controller, or a combination thereof may identify the specific functions of a given interchangeable tip and power the tip accordingly.

The look up table may be any table that lists all of the various functions of the interchangeable tip and a corresponding capacitance, signal measurement, or both of the various interchangeable tips. The look up table may list each of the various functions of the interchangeable tip compared to a signal measurement so that based upon a signal measurement the functions of as particular tip are known. Preferably, the look-up table includes each combination of functions with a corresponding capacitance so that upon installation of an interchangeable tip the generator, the control module, the controller, or a combination thereof may determine all of the capabilities of the interchangeable tip. The look up table may provide the status of one or more switches based upon a comparison of a signal measurement change signal measurement, or a combination of both. For example, when an interchangeable tip is installed the signal measurement may be a first capacitance (e.g., frequency changed caused by a capacitor) and when the switch is actuated the capacitance may increase to a second capacitance indicated that the switch was closed (e.g., a capacitive value of first capacitor was added to a capacitive value of a second capacitor when a switch is closed arriving at the second capacitance). The generator, control module, controller, or a combination thereof may configure, reconfigure, set up, or a combination thereof the system based upon the determined functions of each interchangeable tip. The generator activates one or more functions of the debrider based upon a type of tip from a look up table. The generator may energize and/or control one or more predetermined functions that are loaded into a user interface in the generator so that a predetermined procedure may be produced.

The circuit as discussed herein may be used with a method of detecting an interchangeable tip, identifying a type of interchangeable tip, the function of an interchangeable tip, or a combination thereof. The method steps may be performed in virtually any order or the order discussed herein. The RF generator may provide a signal, power, or both to one or more circuits. The signal, power or both may pass through an identification circuit, a shunt, a control circuit, or a combination thereof. The controller, the microprocessor, the generator, or a combination thereof may monitor the signals, the power, or both in real time. The controller, the microprocessor, the generator, or as combination thereof may compare the signal, the power, or both to one or more predetermined values in a look up table. The controller, the microprocessor, the generator, or a combination thereof may monitor the system, the one or more circuits or both for a shift in capacitance, a shift in impedance, or both and compare the shift to a look up table. The controller, the microprocessor, the generator, or a combination thereof may provide a signal the RF generator to provide power, a signal, or both to no legs of the circuit, one leg of the circuit, both legs of the circuit, one leg of the circuit and a return lead, or a combination thereof. The controller, the microprocessor, the generator; or a combination thereof may monitor in real time for a first shift in frequency, a second shift in frequency, a third shift in frequency, or a combination thereof. For example, a first shift in frequency may represent a tip being installed, a second shift in frequency may represent a switch being activated, a third shift in frequency may represent a switch being closed, a fourth shift in frequency may represent removal of the tip.

FIG. 1 illustrates a microdebrider 2 including a handpiece 4, a tubeset 6, and an interchangeable tip 10 of the teachings herein. The interchangeable tip 10 includes a nose cone 14 having a locking mechanism 12 which prevents rotation of a portion of the stylet 18. The nose cone 14 extends beyond the microdebrider when the interchangeable tip 10 is connected to the microdebrider 2.

Figure 2:
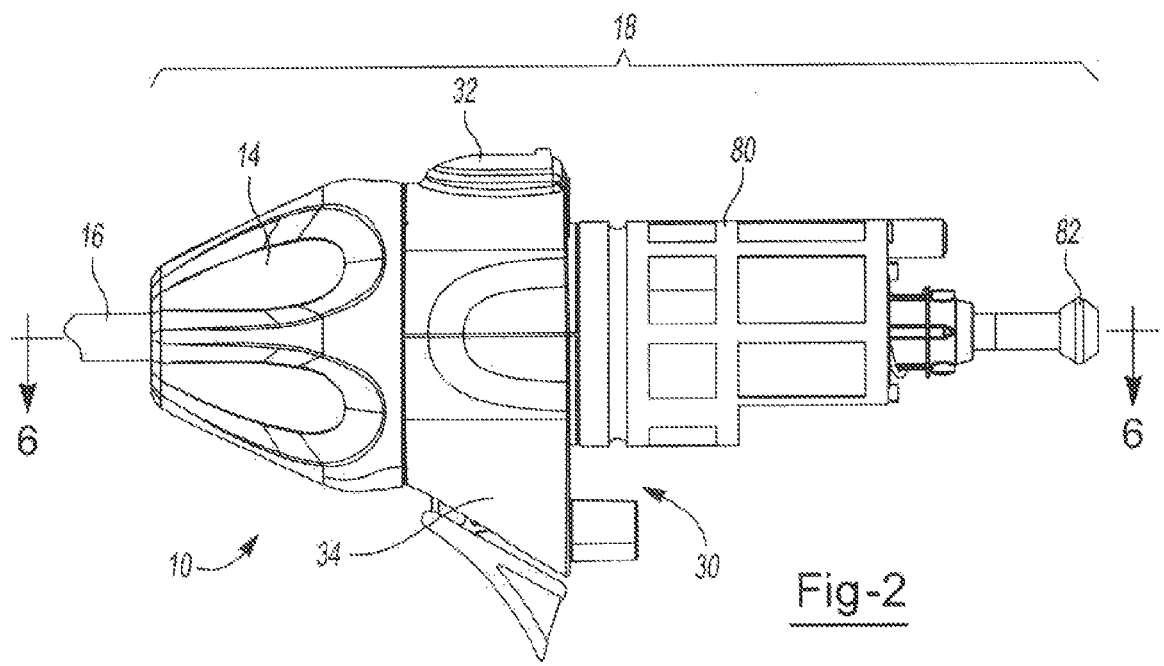
FIG. 2 illustrates a side view of one example of an interchangeable tip.

FIG. 2 illustrates a side view of one example of an interchangeable tip 10 of the teachings herein. The interchangeable tip 10 includes a stylet 16 extending from the nosecone 14 which a user may use to rotate the stylet 16. A blade module 18 having an enclosure 30 is located behind the nose cone 14. The enclosure 30 includes a control enclosure 32 and a connection enclosure 34. A rear portion of the interchangeable tip 10 has a collet 80, an inner tube 82, and blade module 18, and at least a portion of each extend into the handpiece 4 (not shown).

Figure 3:
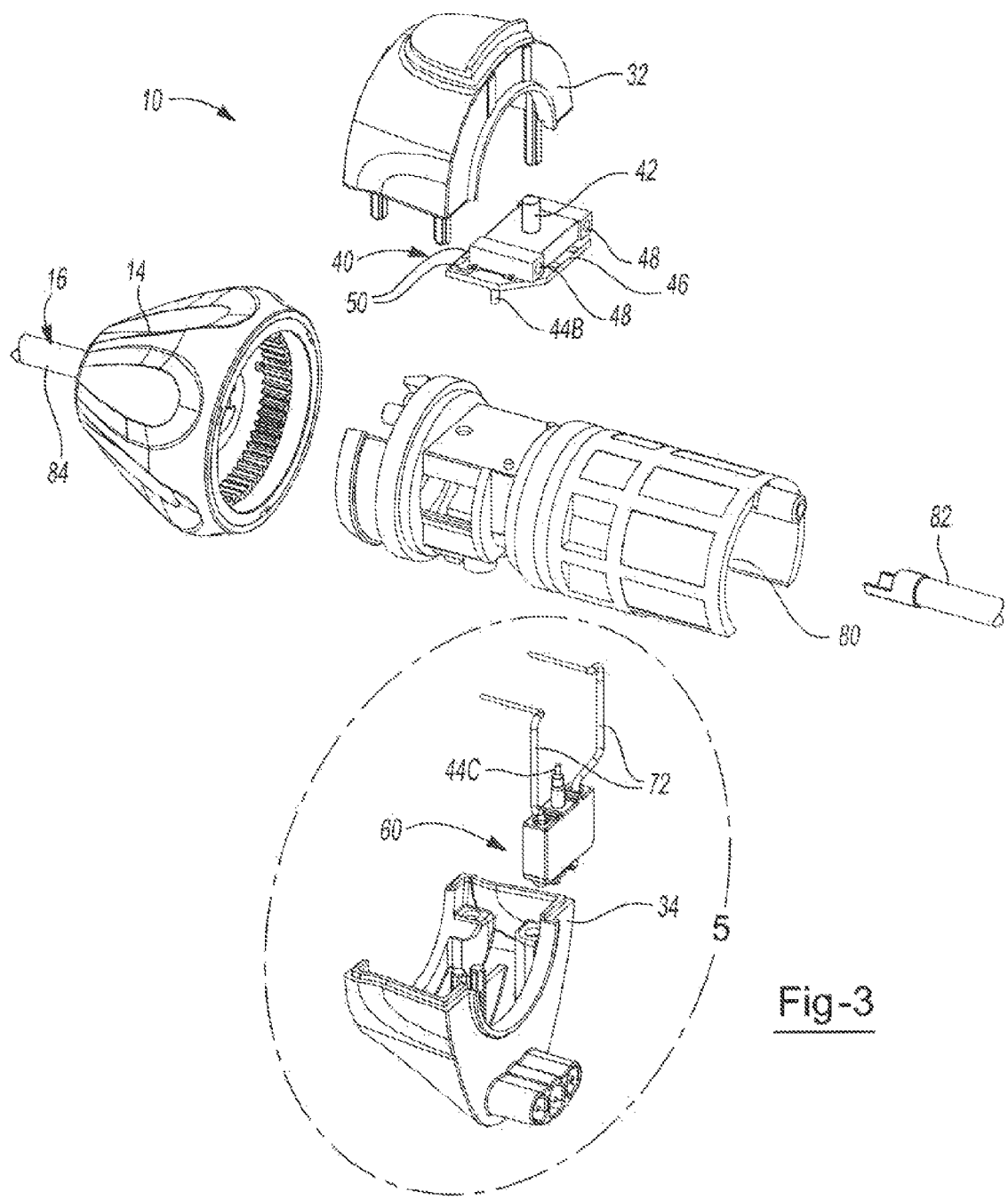
FIG. 3 illustrates a front perspective view of an exploded interchangeable tip.

FIG. 3 illustrates an exploded view of one interchangeable tip 10 taught herein. The interchangeable tip 10 includes a forward portion including a stylet 16 extending from a nose cone 14. An enclosure includes a control enclosure 32 and a connection enclosure 34 which enclose blade circuitry 40 for the interchangeable tip 10. The blade circuitry 40 includes a control button 42, a spring pin 44B, and capacitors 50 mounted on a printed circuit board 46. The connection enclosure 34 houses a connector 60 having a spring pin 440 and wires 72 that extend around the collet 80 and connect to the sockets 48. The rear portion of the interchangeable tip 10 includes a collet 80 with an inner tube 82 removed from the outer tube 84.

Figure 4:
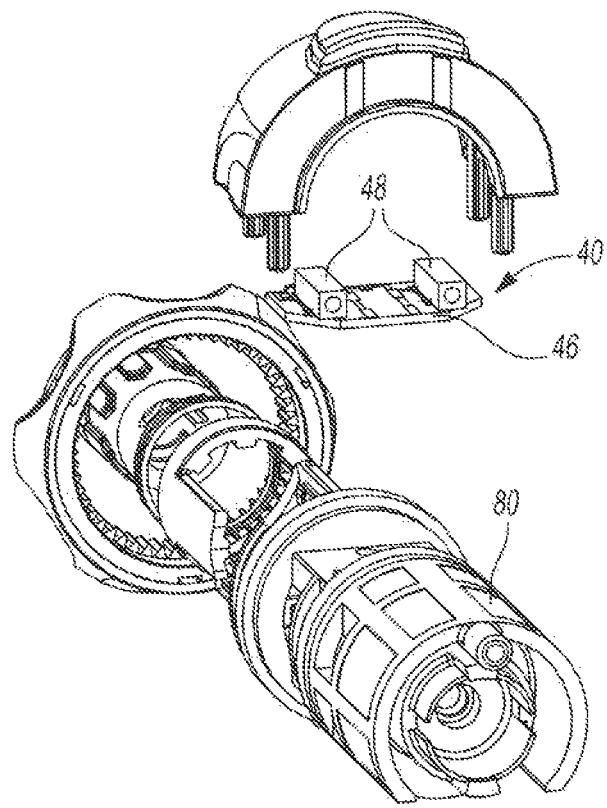
FIG. 4 illustrates a rear perspective view of an exploded interchangeable tip.
Figure 4:
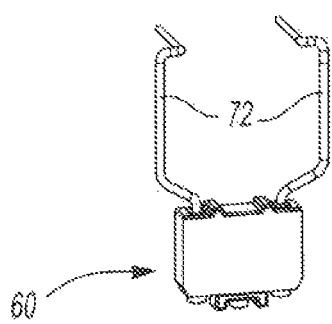
Figure 4:
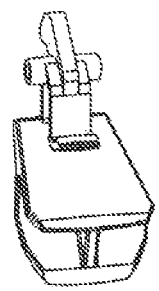

FIG. 4 illustrates a rear perspective exploded. The blade circuitry 40 as illustrated includes a printed circuit board 46 and two sockets 48. The printed circuit board 46 is free of spring pins. A connector 60 having wires 72 that extend around a collet 80 into sockets 48 of the printed circuit board 46 so that the printed circuit board 46 and connector 60 are electrically connected. As illustrated, the connector 60 is free of a spring pin.

Figure 5:
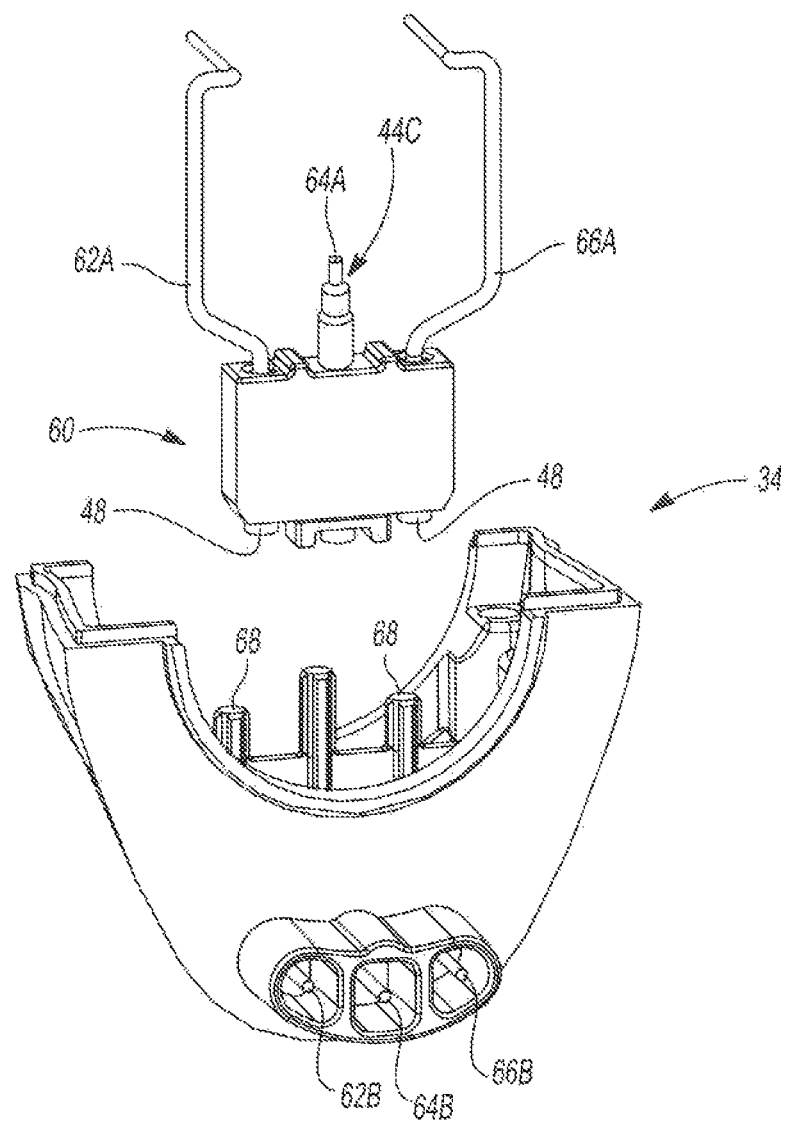
FIG. 5 illustrates a close-up view of a connection enclosure of FIG. 3.

FIG. 5 illustrates a dose up view of the connector 60 of FIG. 3. The connector 60 is housed in and connected to the connection enclosure 34 by connector supports 68. The connector 60 includes two sockets 48. The connection enclosure 34, as illustrated, includes a left connection pin 62B, a middle connection pin 64B, and a right connection pin 66B. The left connection pin 62B, right connection pin 64B, and right connection pin 668 are connected to a left control pin 62A, a middle control pin 64A, and a right connection pin 66A respectively through the connector 60. The left control pin 62A, middle control pin 64A, and right control pin 66A provide power from the handpiece 4 (not shown) of the microdebrider 2 (not shown) to the stylet 16 not shown). The left control pin 62A and right control pin 66A are connected to the connector 60 via the sockets 48 in the connector 60. The middle control pin 64A is a spring pin 44C.

Figure 6A:
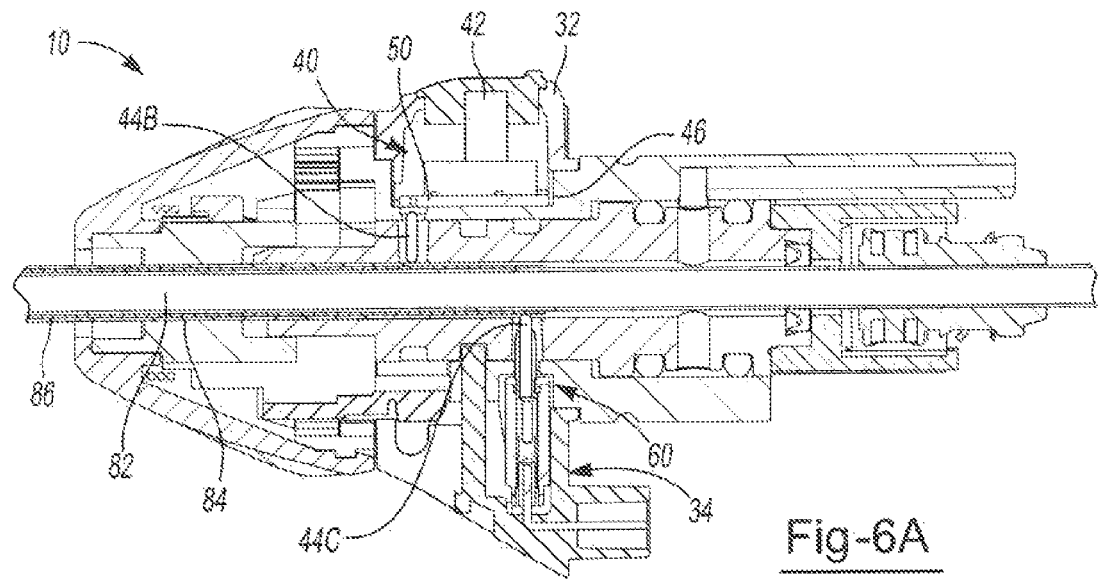
FIGS. 6B-6C illustrate cross sectional views of alternative configurations of interchangeable tip taught herein.

FIG. 6A illustrates a cross-sectional view of the interchangeable tip 10 of FIG. 2. The control enclosure 32 houses blade circuitry 40. The blade circuitry 40 includes a control button 42 connected to a printed circuit board 46. A spring pin 448 extends from the printed circuit board 46 and into contact with the outer tube 84. A capacitor 50 is connected to the printed circuit board 46. An inner tube 82 extends through an intermediate tube 86 and both the inner tube 82 and the intermediate tube 86 extend through the outer tube 84. A connection enclosure 34 is located below the connection enclosure 32. The connection enclosure 34 includes a connector 60 with a spring pin 44C extending from the connector 60 into contact with the intermediate tube 86 so that the interchangeable tip 10 is used to supply bipolar energy.

Figure 6B:
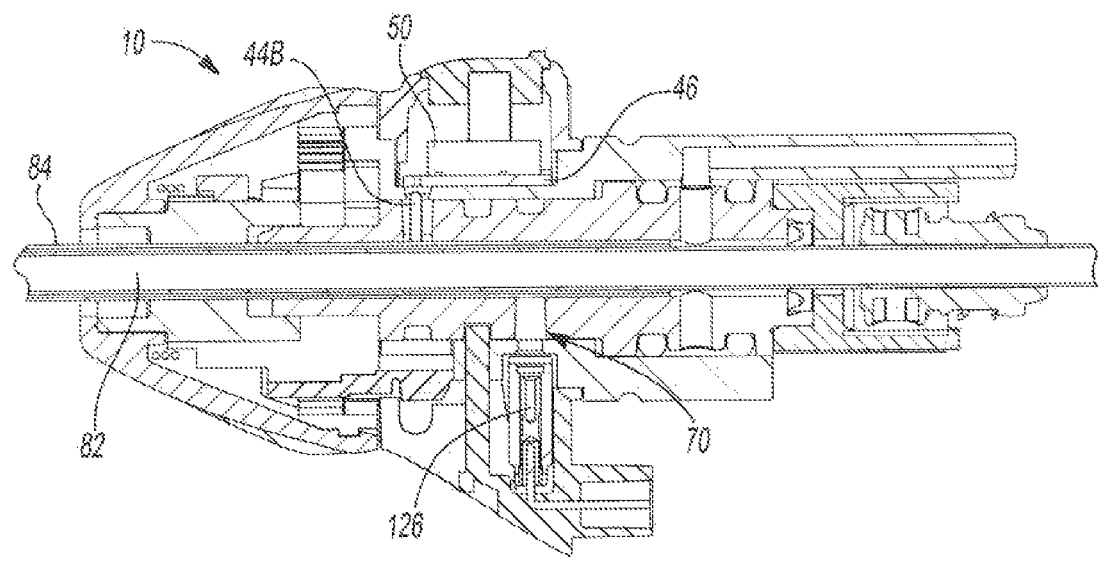
Figure 6C:
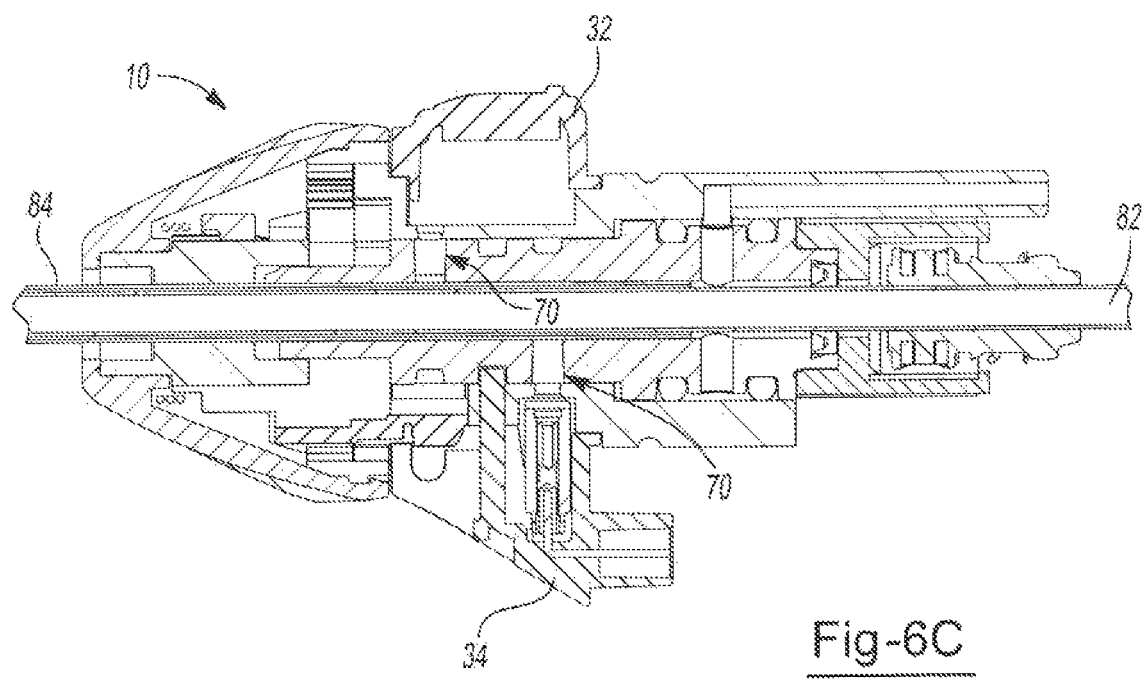

FIG. 6B illustrates cross-sectional of a possible interchangeable tip 10 for supplying monopolar energy. The interchangeable tip 10 includes an open circuit 70 that prevents power from passing from a third input pin 126 to the inner tube 82 extending through the outer tube 83 so that power is only supplied to the outer tube 84 via a spring pin 44B extending from the printed circuit board 46, which includes a capacitor 50. FIG. 6C illustrates a cross-sectional view of a possible interchangeable tip 10 that is nonpolar. The interchangeable tip 10 includes an open circuit 70 in the control enclosure 32 and in the connection enclosure 34 so that no power is supped to the inner tube 82 or the outer tube 84. The control enclosure 32 is free of a printed circuit board with a capacitor so that the interchangeable tip 10 has a zero capacitance.

FIGS. 7A1 and 7A2 illustrate a circuit 100. The circuit 100 is complete when the interchangeable tip 10 is connected to the handpiece 4 and the generator 8. The handpiece 10 includes en identification circuit 150 and a control circuit 160. The identification circuit 150 includes a capacitor 50(I) that generates a signal capacitance for identification and the outer tube 84 for providing power to a stylet (not shown). The control circuit 160 includes a capacitor 50(R) and a switch 120. When the switch 120 is open 120A (FIG. 8A1) the control circuit 160 does not provide power and when the switch is closed 120B (FIG. 8A2) power flows through the control circuit to the outer tube 84 and to the stylet (not shown). Power and signals are provided into the interchangeable tip 10, the control circuit 160, and identification circuit 150 from the headpiece 4 through the first input pin 122 second input pin 124. The control circuit 160 and identification circuit 150 are connected to a detection circuit 170 that includes a control module 172 and an RF generator 174. The handpiece 4 includes a third input pin 126 connected to the intermediate tube 86. When the switch 120 is moved from 120A to 120B power travels through the outer tube 84 and the intermediate tube 86 so that the stylet produces bipolar energy. As illustrated, a second switch 120 is connected to the generator 8 for controlling a different function than the switch 120 on the interchangeable tip 10.

Figure 7B:
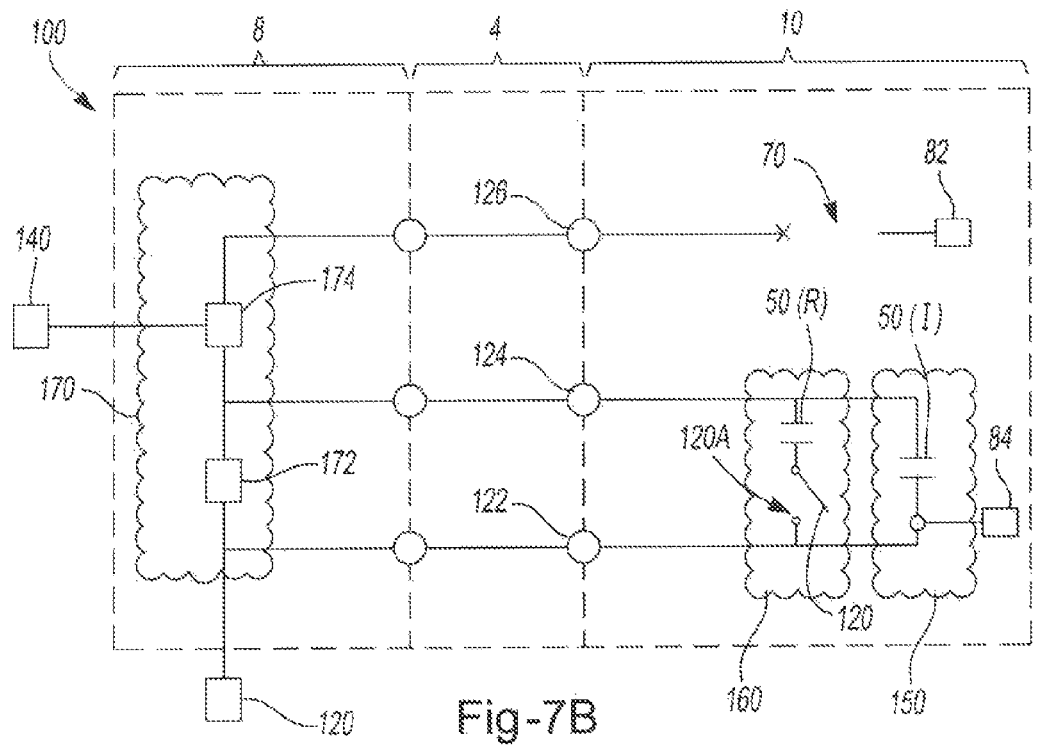
FIG. 7B illustrates circuit diagram representing the configuration of the interchangeable tip of FIG. 6B.

FIG. 7B illustrates a circuit 100. The circuit 100 is complete when the interchangeable tip 10 is connected to the handpiece 4 and the generator 8. The handpiece 10 includes an identification circuit 150 and a control circuit 160. The identification circuit 150 includes a capacitor 50(I) that generates a signal capacitance for identification and provides power to the outer tube 84. The control circuit 160 includes a capacitor 50(R) and a switch 120. When the switch 120 is open 120A the control circuit 16Q does not provide power and when the switch is closed power flows through the control circuit 160 to the outer tube 84 and to the stylet (not shown). Power and signals are provided into the interchangeable tip 10, the control circuit 160, and identification circuit 150 from the handpiece 4 through the first input pin 122 second input pin 124. The control circuit 150 and identification circuit 150 are connected to a detection circuit 170 that includes a control module 172 and an RF generator 174. A return electrode 140 is connected to the generator 8 so that a circuit is complete between the return electrode 140 and the first output 130 for supplying monopolar energy. The handpiece 4 includes a third input pin 126 with an open circuited 70 so that no power flows to the inner tube 82. As illustrated, a second switch 120 is connected to the generator 8 for controlling a different function than the switch 120 on the interchangeable tip 10.

Figure 7C:
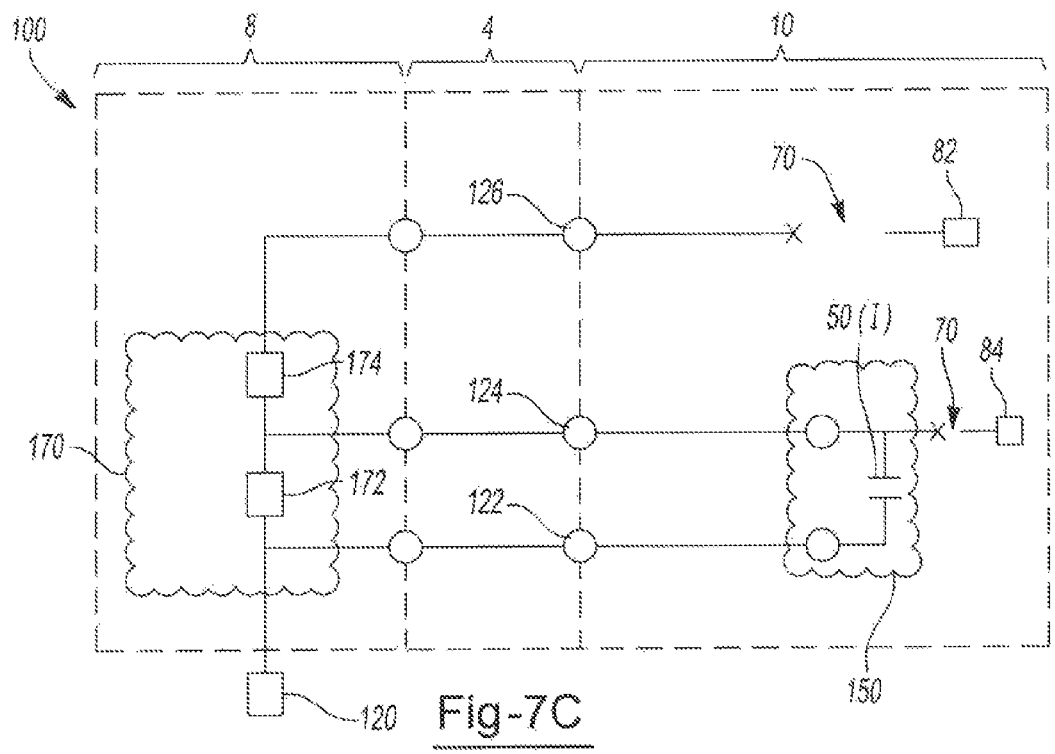
FIG. 7C illustrates a circuit diagram representing the configuration of the interchangeable tip of FIG. 6C.

FIG. 7C illustrates a circuit 100. The circuit is complete when the interchangeable tip 10 is connected to the handpiece 4 and the generator 8. The handpiece 10 includes an identification circuit 150 and is free of a control circuit. The identification circuit includes a capacitor 50(I) so that the function of the interchangeable tip 10 can be identified by the detection circuit 170. An open circuit 70 is located between the identification circuit 150 and the outer tube 84 so that power does not flow from the identification circuit 150 to the outer tube 84. The identification circuit 150 is connected to the detection circuit 170 by a first input pin 122 and a second input pin 124. The detection circuit 170 includes a control module 172 and an RF generator 174 for providing signals and/or power through the circuit 100. A third input pin 126 is connected to the generator 8 and has en open circuit 70 so that power does not flow from the third input pin 126 to the inner tube 82. A second switch 120 is connected to is connected to the generator 8 for controlling a function.

Figure 7D:
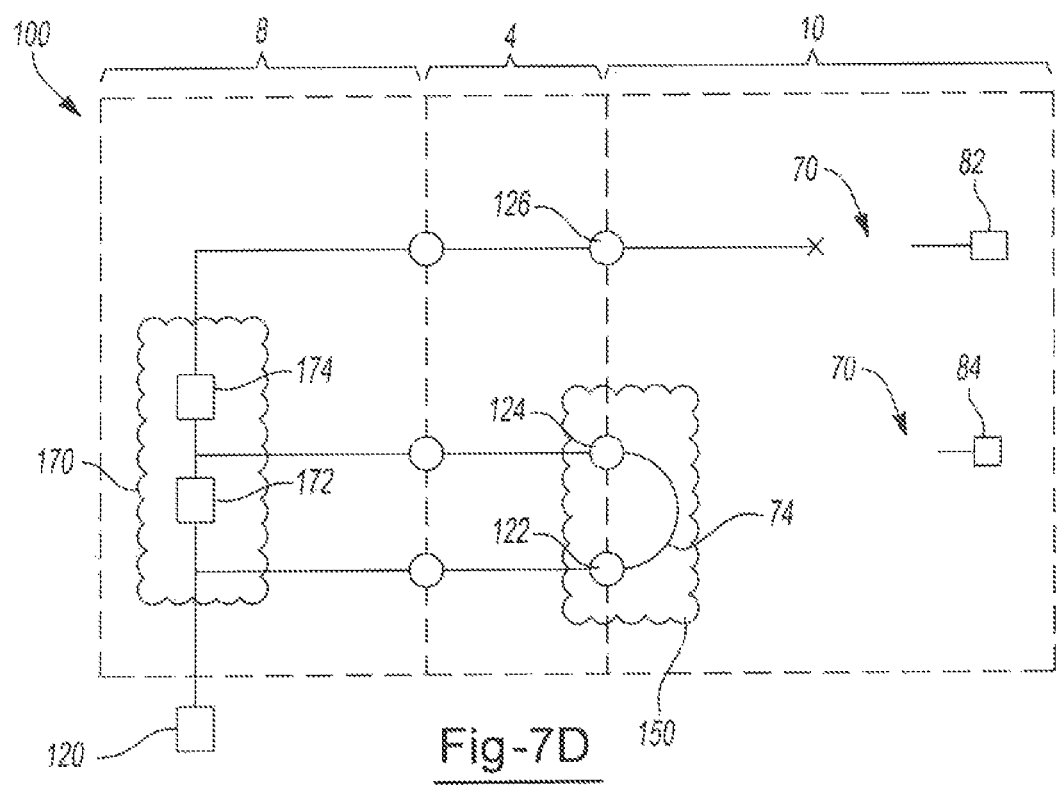
FIG. 7D illustrates a circuit diagram representing another possible configuration of the interchangeable tip.

FIG. 7D illustrates a circuit 100. The circuit is complete when the interchangeable tip 10 is connected to the handpiece 4 and the generator 8. A first input pin 122 and a second input pin 124 are electrically connected and signally connected to the interchangeable tip 10 and are connected together by a shunt 74 so that an identification circuit 150 is formed and power does not flow to the outer tube 84. The identification circuit 150 is connected to a detection circuit 170 that includes a control module 172 and an RF generator 174. The generator 8 is connected to a switch 120 for controlling a function of the interchangeable tip 10. A third input pin 126 is connected to the interchangeable tip 10 and includes an open circuit 70 so that power is not supplied to the inner tube 82.

Any numerical values recited herein include all values from the lower value ter the upper value in increments of one unit provided that there is a separation of at least 2 units between any lower value and any higher value. As an example, if it is stated that the amount of a component or a value of a process variable such as, for example; temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30" inclusive of at least the specified endpoints.

The disclosures of all articles and references including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not, restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An interchangeable tip comprising,
   a. a stylet;
   b. a blade module including;
      i. a connection enclosure and
      ii. a control enclosure including two or more pins;

wherein a signal across the two or more pins has a capacitance of zero for determining a type of the interchangeable tip.

2. The interchangeable tip of claim 1, wherein the connection enclosure is free of any spring pins for providing electrical power to the stylet.

3. The interchangeable tip of claim 1, wherein the two or more input pins are shunted so that the two or more pins are directly connected.

4. The interchangeable tip of claim 1, wherein an identification circuit is formed by extending a shunt between the two or more pins, and the two or more pins extend between the control enclosure and the connection enclosure.

5. The interchangeable tip of claim 4, wherein the connection enclosure includes a connector and the two or more pins extend into the connector.

6. The interchangeable tip of claim 1, wherein the connection enclosure includes one or more plugs and each of the one or more plugs include one or more connection pins.

7. The interchangeable tip of claim 6, wherein the one or more plugs are configured to create a connection between the interchangeable tip and a handpiece.

8. The interchangeable tip of claim 7, wherein the one or more connection pins are each in electrical communication, signal communication, or both with one of the two or more pins so that an identification circuit is formed.

9. The interchangeable tip of claim 6, wherein the two or more pins are each connecting one of the one or more connection pins on a first end and the two or more pins are connected together on a second end by a shunt.

10. The interchangeable tip of claim 9, wherein the shunt prevents power from flowing from the two or more pins to the stylet.

11. The interchangeable tip of claim 1, wherein an identification circuit is created by a connector electrically connecting the two or more pins.

12. An interchangeable tip comprising:
 a. a stylet;
 b. a blade module including;
  i. a connection enclosure and
  ii. a control enclosure including two or more pins;
wherein a signal across the two or more pins has a capacitance of zero;
wherein the blade module is free of a printed circuit board.

13. The interchangeable tip of claim 12, wherein the connection enclosure is free of any spring pins for providing electrical power to the stylet.

14. The interchangeable tip of claim 12, wherein the two more pins are shunted so that the two or more pins are directly connected.

15. The interchangeable tip of claim 12, wherein an identification circuit is formed by extending a shunt between the two or more pins.

16. The interchangeable tip of claim 12, wherein connection enclosure includes a connector and the two or more pins extend into the connector and the connection enclosure includes one or more plugs and each of the one or more plugs include one or more connection pins.

17. The interchangeable tip of claim 12, wherein the connection enclosure includes one or more plugs and each of the one or more plugs include one or more connection pins and the one or more plugs are configured to create a connection between the interchangeable tip and a handpiece:
 wherein the two or more pins are each connecting one of the one or more connection pins on a first end and the two or more pins are connected together on a second end by a shunt; and
 wherein the one or more connection pins are each in electrical communication, signal communication, or both with one of the two or more pins so that an identification circuit is formed.

18. The interchangeable tip of claim 12, wherein an identification circuit is created by a connector electrically connecting the two or more pins.

19. The interchangeable tip of claim 18, wherein the shunt prevents power from flowing from the two or more pins to the stylet.

20. A method comprising:
 a. inserting an interchangeable tip into a handpiece, wherein the interchangeable tip comprises:
  i. a stylet;
  ii. a blade module including:
   1. an enclosure that electrically connects, signally connects, or both the interchangeable tip to a power source, a signal source, or both; and
   2. blade circuitry having: one or more switches for controlling operation one or more functions of the interchangeable tip;
 b. providing a signal to the handpiece and the interchangeable tip; and
 c. detecting a capacitance generated by the interchangeable tip in response to the step of providing the signal;
 wherein the step of detecting determines whether the interchangeable tip is configured to provide bipolar energy, monopolar energy, no power, or a combination thereof.

21. The method of claim 20, wherein the method includes a step of comparing the capacitance generated by the interchangeable tip to a look up table in order to determine a configuration of the interchangeable tip.

22. The method of claim 20, wherein the method includes a step of determining whether the interchangeable tip is configured to provide forward rotation, reverse rotation, oscillating rotation, reciprocating, high speed rotation, low speed rotation, non-rotational or a combination thereof.

23. The method of claim 22, wherein the handpiece is connected to a generator and the method includes a step of configuring, reconfiguring, setting up, or a combination thereof the generator based upon the determined configuration of the interchangeable tip.

24. The method of claim 23, wherein the method includes a step of the generator energizing and/or controlling the one or more of functions of the determined configuration.

25. The method of claim 24, wherein the blade module includes connection enclosure and a control enclosure, and the control enclosure includes two or more pins and the capacitance across the two or more pins is zero.

26. The method of claim 20, wherein the capacitance is determined by monitoring a change in the signal provided to the handpiece when the interchangeable tip is inserted into the handpiece.

* * * * *